United States Patent [19]
Johnson et al.

[11] Patent Number: 5,621,123
[45] Date of Patent: *Apr. 15, 1997

[54] CYCLIC HYDROCARBONS WITH AN AMINOALKYL SIDECHAIN

[75] Inventors: Roy A. Johnson, Kalamazoo; Gordon L. Bundy, Portage; Gilbert A. Youngdale, Portage; Douglas R. Morton, Portage; Donald P. Wallach, deceased, late of Kalamazoo; Vera M. Wallach, legal representative, Richland, all of Mich.

[73] Assignee: The Upjohn Company, Kalamazoo, Mich.

[*] Notice: The portion of the term of this patent subsequent to Feb. 16, 2010, has been disclaimed.

[21] Appl. No.: 247,169

[22] Filed: May 20, 1994

Related U.S. Application Data

[62] Division of Ser. No. 976,751, Nov. 16, 1992, Pat. No. 5,334,712, which is a division of Ser. No. 657,721, Feb. 20, 1991, Pat. No. 5,196,542, which is a division of Ser. No. 394,396, Aug. 15, 1989, abandoned, which is a division of Ser. No. 117,851, filed as PCT/US86/02116, Oct. 7, 1986, Pat. No. 4,917,826, which is a continuation-in-part of Ser. No. 843,120, Mar. 24, 1986, abandoned, which is a continuation-in-part of Ser. No. 788,995, Oct. 18, 1985, abandoned.

[51] Int. Cl.$^6$ .................................................. C07J 41/00
[52] U.S. Cl. ............................................ 552/522; 552/554
[58] Field of Search ................................. 540/112, 117; 552/522; 564/460

[56] References Cited

U.S. PATENT DOCUMENTS

| | | | |
|---|---|---|---|
| 3,084,156 | 4/1963 | Counsell et al. | |
| 3,107,255 | 10/1963 | Counsell et al. | |
| 3,284,474 | 11/1966 | Klimstra. | |
| 3,284,475 | 11/1966 | Klimstra. | |
| 3,326,758 | 6/1967 | Irmscher et al. | 552/522 |
| 3,370,070 | 2/1968 | Klimstra. | |
| 3,639,598 | 2/1972 | Klimstra. | |
| 4,239,780 | 12/1980 | Wallach | 424/330 |
| 4,330,539 | 5/1982 | Sleigh et al. | 552/522 |
| 5,075,434 | 12/1991 | Youngdale | 540/106 |

FOREIGN PATENT DOCUMENTS

| | | |
|---|---|---|
| 1074578 | 12/1963 | European Pat. Off. . |
| 1337759 | 7/1960 | France. |
| 1421230 | 11/1965 | France. |
| 1187236 | 2/1965 | Germany. |
| 1074578 | 7/1967 | United Kingdom. |

OTHER PUBLICATIONS

W. Vogt, Advances in Prostaglandins and Thromboxane Research, 3:89–95 (1978).
P.C. Isakson et al, Advances in Prostaglandin and Thromboxane Research, 3–113–120 (1978).
N.A. Plummer et al, Journal of Investigative Dermatology, 68:246 (1977).
B.B. Vargaftig, J. Pharm. Pharmacol., 29:222–228 (1977).
R.J. Flower et al, Nature, 278:456–459 (1979).
L. Kaplan et al, Proc. Natl. Acad. Sci., 75:2955–2988 (1978).
E. Vallee et al, J. Pharm. Pharmacol., 31:588–592 (1974).
M. Roberts et al., J. of Biol. Chem., 252:2405–2411 (1977).
G.J. Blackwell et al, British J. Pharmacy, 62:79–89 (1978).
D.P. Wallach et al, Bioch. Pharmacol., 30:1315–1324 (1981).
L.J. Griggs, "Part I. Synthetic Approaches to 5– and 16–Thiaestrone. Part II. Estrone With a Diazacholesterol Side Chain", University of Michigan (1965).
P.D. Klimstra et al., J. Med. Chem., 9:323–326 (1966).
Klimstra et al. Hypocholesterolenic Agents VI, May, 1966 pp. 323–325.
Grant and Hackh's Chemical Dictionary (New York, McGraw–Hill, 1987) p. 14.
Vogt, W., "Role of Phospholipase $A_2$ in Prostaglandin Formation", Advances in Prostaglandins and Thromboxane Research, 3, p. 89 (1978).
Isakson, P.C. et al., "Lipases and Prostaglandin Biosynthesis", Advances in Prostaglandin and Thromboxane Research, 3, p. 113, (1978).
Plummer, N.A., et al., "Activation of the Arachidonate Cascade in Human Skin Inflamed by Irradiation with UVC and the Effects of Indomethacin", abstracted in Journal of Investigative Dermatology, 68, p. 246 (1977).
Vargaftig, B.B., "Carrageenan and thrombin trigger prostaglandin synthetase-independent aggregation of rabbit platelets: inhibition by phospholipase $A_2$ inhibitors", J. Pharm. Pharmacol., 29, pp. 222–228 (1977).
Flower, R.J. and Blackwell, G.J., "Anti–inflammatory steroids induce biosynthesis of a phospholipase $A_2$ inhibitor which prevents prostaglandin generation", Nature, 278, pp. 456–459 (1979).
Kaplan, K.L., et al., "Low concentrations of indomethacin inhibit phospholipase $A_2$ of rabbit polymorphonuclear leukocytes", Proc. Natl. Acad. Sci., 75, pp. 2955–2988 (1978).
Vallee, E., et al., "Anti–inflammatory and platelet anti–aggregant activity of phospholipase–$A_2$ inhibitors", J. Pharm. Pharmacol., 31, pp. 588–592 (1974).
Roberts, M.F., et al., "Chemical Modification of the Histidine Residue in Phospholipase $A_2$", J. of Biol. Chem., 252, pp. 2405–2411 (1977).

(List continued on next page.)

Primary Examiner—Mukund J. Shah
Assistant Examiner—Pavanaram K. Sripada
Attorney, Agent, or Firm—Thomas A. Wootton

[57] ABSTRACT

Provided are cyclic hydrocarbons of Formula I

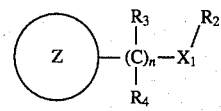

with an aminoalkyl sidechain that are useful for treating phospholipase A2 mediated conditions, diabetes, and obesity.

4 Claims, No Drawings

OTHER PUBLICATIONS

Blackwell, G.J., et al., "Phospholipase $A_2$ Activity of Guinea–Pig Isolated Perfused Lungs: Stimulation, and Inhibition by Anti–Inflammatory Steroids", British J. Pharmacy, 62, pp. 79–89 (1978).

Wallach, D.P. and Brown, V.J.R., "Studies on the Arachidonic Acid Cascade–I", Bioch. Pharmacol., 30, pp. 1315–1324 (1981).

Doctoral thesis, L.J. Griggs, "Part I. Synthetic Approaches to 6– and 16–Thiaestrone. Part II. Estrone with a Diazacholesterol Side Chain," University of Michigan (1965).

Klimstra, P.D., et al., "Hypocholesterolemic Agents. VI. A– and B–Ring–Modified Azacholesterols", J. Med. Chem., 9, pp. 323–326 (1966).

CYCLIC HYDROCARBONS WITH AN AMINOALKYL SIDECHAIN

CROSS REFERENCE TO RELATED APPLICATIONS

This application is a division of application Ser. No. 07/976,751, filed 16 Nov. 1992, issued as U.S. Pat. No. 5,334,712 on 02 Aug. 1994, which was a division of application Ser. No. 07/657,721, filed 20 Feb. 1991, issued as U.S. Pat. No. 5,196,542 on 23 Mar. 1993, which was a division of application Ser. No. 07/394,396, filed 15 Aug. 1989, now abandoned, which was a division of application Ser. No. 07/117,851, filed 16 Jun. 1987, now U.S. Pat. No. 4,917,826, which was the continuing national phase of International Patent Application No. PCT/US86/02116, International Filing Date, 7 Oct. 1986, which was a continuation-in-part of patent application Ser. No. 06/843,120, filed 24 Mar. 1986, now abandoned, which was a continuation-in-part of patent application Ser. No. 06/788,995, filed 18 Oct. 1985, now abandoned.

FIELD OF INVENTION

This invention relates to novel compositions of matter. More particularly, the invention relates to cyclic hydrocarbons with an aminoalkyl sidechain that are useful for inhibiting phospholipase A2 and for treating diabetes and obesity.

INFORMATION DISCLOSURE

The important role of phospholipase A2 in mammalian metabolism through the formation of prostaglandins is now well known. See W. Vogt, Advances in Prostaglandins and Thromboxane Research, 3, p. 89 (1978); P. C. Isakson, et al., Advances in Prostaglandin and Thromboxane Research, 3, page 113, (1978). Phospholipase A2 is responsible for the hydrolysis of arachidonic acid-containing phospholipids, thereby providing substrate for the multiple enzymes of the arachidonic acid cascade.

The products of the arachidonic acid cascade are varied. These products include prostaglandins, thromboxanes, leukotrienes, and other hydroxylated derivatives of arachidonic acid. All of the foregoing are referred to as "eicosanoids." While generally the products of the cascade are beneficial, in certain disease processes and other conditions the excessive production of eicosanoids induces deleterious consequences such as inflammation (see paper by N. A. Plummer, et al.; abstracted in Journal of Investigative Dermatology, 68, p. 246 (1977)); erythema (N. A. Plummer, supra); platelet aggregation (B. B. Vargaftig, J. Pharm. Pharmacol., 29, pp. 222–228 (1977)); and the release of SRS-A (slow reacting substance-anaphylaxis), a known mediator of allergic responses. The inhibition of phospholipase A2 prevents these and similar conditions mediated by the action of this enzyme.

Some inhibitors of phospholipase A2 are known. R. J. Flower and G. J. Blackwell have shown that certain anti-inflammatory steroids induce biosynthesis of a phospholipase A2 inhibitor which prevents prostaglandin generation. See Nature, 278, p. 456 (1979). These steroids are not direct inhibitors of phospholipase A2, but rather stimulate the synthesis of a phospholipase inhibiting factor called lipocortin, lipomodulin, or macrocortin.

Some examples of direct phospholipase A2 inhibition are known. Indomethacin, a drug with anti-inflammatory properties, has been shown to inhibit phospholipase A2 enzymes. See K. L. Kaplan, et al., Proc. Natl. Acad. Sci., 75, pp. 2955–2988 (1978).

Indomethacin has been shown to inhibit phospholipase A2 enzymes, isolated respectively from the venoms of Russell's Viper, Crotalus adamanteus, and bee, and from pig pancreas. Certain local anesthetics have been shown to inhibit phospholipase A2 activity by competing with calcium ion, which appears to be a requirement for phospholipase activity. See W. Vogt, Advances in Prostaglandin and Thromboxane Research, 3, p. 89 (1978) and E. Vallee et al., J. Pharm. Pharmacol., 31, pp. 588–92 (1974). Bromphenacyl bromide has been shown to inhibit phospholipase A2 by acylating a histidine residue which is at the active site of the enzyme. See M. Roberts, et al., J. of Biol. Chem., 252, pp. 2405–2411 (1977). R. Blackwell, et al., British J. Pharmacy, 62, p. 79–89 (1978) has disclosed that mepacrine inhibits the activity of phospholipase A2 derived from perfused guinea pig lung. Certain butyrophenones are disclosed as phospholipase A2 inhibitors in U.S. Pat. No. 4,239,780. D. P. Wallach and V. J. R. Brown, Bioch. Pharmacol., 30, pp. 1315–24 (1981) also refer to several compounds that inhibit phospholipase A2.

Some of the steroids employed for synthesizing compounds of the present invention and useful in some of the methods of treatment are known. See the doctoral thesis, L. J. Griggs, "Part I. Synthetic Approaches to 5- and 16-Thiaestrone. Part II. Estrone with a Diazacholesterol Side Chain," University of Michigan (1965). These compounds are stated therein to be potential hypocholesterolemic agents. U.S. Pat. No. 3,370,070 discloses similar steroid compounds which are useful as hypocholesterolemic agents and as antibacterial, anti-protozoal, and anti-algal agents.

Some of the steroidal compounds herein are also referred to in U.S. Pat. No. 3,284,475 and in P. D. Klimstra, et al., "Hypocholesterolemic Agents. VI. A- And B-Ring-Modified Azacholesterols", J. Med. Chem., 9, pp. 323–26 (1966).

The present invention also relates to antidiabetic agents. Hyperglycemia refers to a condition commonly found in patients suffering from mature-onset diabetes mellitus and other diseases in which impairment of pancreatic function is a consequence thereof. Accordingly, hyper-glycemic patients are those exhibiting elevated serum glucose levels. Failure to adequately control such elevated serum glucose levels has been associated in such patients with untoward cardiovascular effects (myocardioischemia, stroke, and peripheral vascular diseases), lethargy, coma, blindness, kidney failure and even death.

While conventional treatment for these hyperglycemic conditions may include diet (e.g. restriction of carbohydrate intake) and insulin injection, one important means of treating such patients is with oral antidiabetic agents such as those disclosed herein.

SUMMARY OF THE INVENTION

The present invention relates to cyclic hydrocarbons of formula I wherein:

A compound of the formula

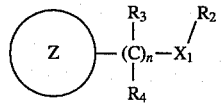

wherein:

(I) Z is

[steroid structure with R20, CH3, A, D labels]

wherein [cyclohexane with A, D] is a. [structure with R5O], b. [structure with O], c. [structure with O, D], d. [structure with D, E], e. [structure with X2, X3, J], or f. [pyridine with G]

(1) wherein D is
(a) H, (b) CH₃, or (c) no bond;
(2) wherein E and J are
(a) H, (b) R₅O—, or (c) —N(CH₃)—(CH₂)₃—N(CH₃)₂ with the provisos that when E is H, the 5,6 bond is saturated and that when J is H, X₂ and X₃ are H;
(3) wherein G is
(a) nothing, or (b)→O;
(4) wherein R₅ is
(a) H, (b) C1–C3 alkyl, (c) benzyl, (d) acyl, (e) C(O)H, (f) HOCH₂CH(OH)CH₂, (g) R₄—OC—(O)CH₂;
(5) wherein X₂ and X₃ are
(a) H, (b) NO₂, (c) NH₂, (d) OH, or (e) halogen;
A. C8–C20 cycloalkyl, C. 2- or 4-cyclohexylcyclohexyl, D. 4-bicyclohexylcyclohexyl, E. 4-bicyclohexenylcyclohexyl, F. 3-cyclopentylcyclopentyl, G. 1-, 3- or 4-(2-decahydronaphthyl)cyclohexyl, H. 1- or 2-tetradecahydroanthracenyl, I. 2- or 3-tetradecahydrophenanthrenyl, J. 1- or 2-dodecahydro-1H-phenallyl, K. 1- or 2 hexadecahydropyrenyl, L. 1- or 2-octadecahydrotriphenylenyl, M. 1- or 2-octadecahydrochrysenyl, N. 1- or 2-octadecahydronaphthacenyl, O. phenylcyclohexyl, P. adamantyl, Q. pyrenyl, R. 3-fluorobiphenylyl, or S. 1- or 2- decalinyl;
II. wherein X₁ is
A. NR₁, B. NR₁R₁₃, C. N⁺·R₁·R₁·R₁₃ X⁻, or D. —O—C(O)—CH((CH₂)₃— NH₂)(NH₂);
1. wherein X⁻ is a pharmaceutically acceptable anion;
2. wherein R₁₃ is
a. methyl, or b.→O;
3. wherein R₁ is
a. H, b. —CHO, c. —COCH₃, d. C1–C6 alkyl, e. —(CH₂)ᵣ— CO₂R₄, f. —CH₂CH=CH₂, g. —(CH₂)ₚ—X₄, h. —(CH₂)ₘ— N(R₆)(R₇), i. —(CH₂)ₚ—O(CH₂)ₚ—N(R₆)(R₇), j. —(CH₂)ₚ— —Y—C(=NH)—NH₂, k. —(CH₂)q—CH(NH₂)— COOR₁₆, l. —(CH₂)ₚ—N=C(R₁₄)(R₁₅), m. —(CH₂)ₚ—NH—C(CH₃)₂—CH₂—C(O)—CH₃, n. —(CH₂)ᵣ—[phenyl with X₇, X₈], o. —(CH₂)ᵣ—[pyridine with R₈], p. —(CH₂)ᵣ—[imidazole with R₉], q. —(CH₂)ₚ—N[imidazole], r. [phenyl with R₈, X₅, (CH₂)ᵣ], s. —(CH₂)ₚ—N[lactam (CH₂)₂₋₉], t. —(CH₂)ᵣ—CH—CH₂ [epoxide], u. —CH₂—[benzimidazole], v. —CH₂—[furan], w. —[phenyl with X₇, X₈], x. N[tetrazole]—(CH₂)ᵣ, y. [thiazole], z. [thiazole], a. [pyrimidine], b. [pyridine with R₈], c. —CH₂—[thiazolidinedione]

(1) wherein R₄ is
(a) H, or (b) C1–C2 alkyl;
(2) wherein X₄ is
(a) OH, (b) OCH₃, (c) OC₂H₅, (d) OCH₂CH₂OH, (e)OTs, (f)OMs, (g)Cl, (h) Br, (j) aziridinyl, or (k)

N⁺(CH₃)₂
|
R₁₂   X⁻ i) wherein R₁₂ is
ii)(a) C1–C2 alkyl, ii)(b) benzyl, ii)(c) CH₂Cl, ii)(d)→ O, ii)(e) CH₂COOC₂H₅, or ii)(f) C3–C18 straight chain alkyl;
(3) wherein R₆ is
(a) H, (b) C1–C13 alkyl, (c) benzyl, (d) phenyl, (e)— (CH₂)ₚ—N(R₁₀(R₁₁), (f)C(O)CH₃, (g)

(g) —(CH₂)ₚ—N[ring with X₆], (h) [pyridine with NO₂] or

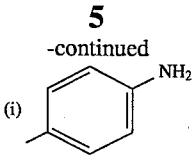
(i)

i) wherein $R_{10}$ and $R_{11}$ are
i)(a) H, i)(b) C1–C2 alkyl, or i)(c) $(CH_2)_3$—$NH_2$;
ii) wherein $R_{10}$ and $R_{11}$ together are

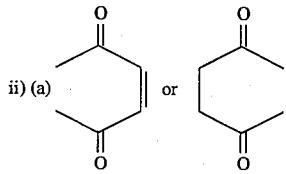

(4) wherein $R_7$ is
(a) H, (b) C1–C2 alkyl, (c) —$(CH_2)_p$—$N(R_{10})(R_{11})$, or (d) CHO;

(5) wherein $R_6$ and $R_7$ together are

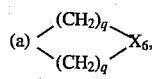

i) wherein $X_6$ is
i)(a) O, i)(b) NH, i)(c) $NCH_3$, or i)(d) $N(CH_2)_qNH_2$;

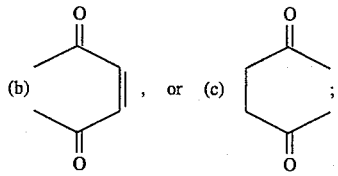

(6) wherein Y is
(a) NH, or (b) S;

(7) wherein $R_8$ is
(a) H, (b) C1–C2 alkyl, (c) $OCH_3$, (d) $NO_2$, (e) $NH_2$, (f) $NHCOCH_3$, (g) CN, (h) $CH_2NH_2$, (i) $CONH_2$, (j) Cl, (k) Br, or (l) $COOCH_3$;

(8) wherein $R_9$ is
(a) H, (b) methyl, (c) benzyl, or (d) —$(CH_2)_pN(R_{10})(R_{11})$;

(9) wherein $R_{14}$ is
(a) H, or (b) C1–C6 alkyl;

(10) wherein $R_{15}$ is C1–C6 alkyl;

(11) wherein $R_{16}$ is
(a) H, or
(b) C1–C4 alkyl;

(12) wherein $X_7$ and $X_8$ are the same or different and are
(a) H, (b) $CH_3$, (c) $CF_3$, (d) halogen, (e) OH, (f) $OCH_3$, (g) $NO_2$, (h) $NH_2$, (i) $NHR_4$, (j) $NR_4R_4$, (k) —$CH_2NH_2$, (l) —$CH_2NHR_2$, (m) —$SO_2N(R_3)(R_4)$, (n) —$CO_2R_4$, (o) $CON(R_3)(R_4)$, (p) $CH_2N(R_3)(R_4)$, or (q) tetrazolyl;

III. wherein $R_2$ is
A. H, B. C1–C4 alkyl, C. benzyl, D. —$(CH_2)_p$—$N(R_6)(R_7)$,

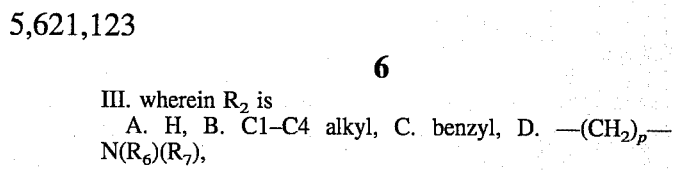

$N(\rightarrow O)(R_6)(R_7)$, H. —$(CH_2)_pN^+(CH_2$—$Ph)(R_6)(R_7)$, or I. —$(CH_2)_pN^+(CH_3)(R_6)(R_7)$, J. nothing;

IV. wherein $R_1$ and $R_2$ together are

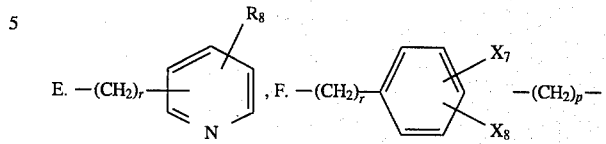

1. wherein $X_5$ is
a. O, b. NH, c. $NCH_3$, or d. S;

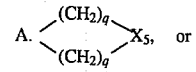

2. wherein $X_9$ is
a. O, b. NH, or c. $NCH_3$;

V. wherein $R_3$ is
A. H, B. C1–C2 alkyl, or C. $CH_2OH$;

wherein m is 2–8;
wherein n is 0–1;
wherein p is 2–8;
wherein q is 2–4;
wherein r is 1–8;
wherein s is 2–8; and
pharmacologically acceptable salts thereof;

with the proviso that when n is 1 and $R_1$ is —$(CH_2)_m$—$N(R_6)(R7)$ wherein m is 2 or 3 and $R_2$ is H or $CH_3$, or when $R_2$ is —$(CH_2)_m$—$N(R_6)(R7)$ wherein m is 2 or 3 and $R_1$ is H, $CH_3$, CHO, or $CH_3CO$, then $R_6$ and $R_7$ cannot both be hydrogen, methyl, or ethyl;

and with the proviso that when n is 0 and $R_1$ is —$(CH_2)_m$—$N(R_6)(R7)$ wherein m is 2 or 3 and $R_2$ is H or $CH_3$, or when $R_2$ is —$(CH_2)_m$—$N(R_6)(R7)$ wherein m is 2 or 3 and $R_1$ is H, $CH_3$, CHO, or $CH_3CO$, then $R_6$ and $R_7$ cannot both be hydrogen, methyl, or ethyl, propyl, or isopropyl;

and with the proviso that when n is 0 and one of $R_1$ and $R_2$ is —$(CH_2)_m$—$N(R_6)(R7)$ wherein m is 3, and the other is H or methyl, then $R_6$ and $R_7$ cannot be H or methyl;

and with the proviso that when n is 0 and X1 is $NR_1$, then $R_1$ cannot be CHO when $R_2$ is H;

for each of the foregoing provisos, Z is

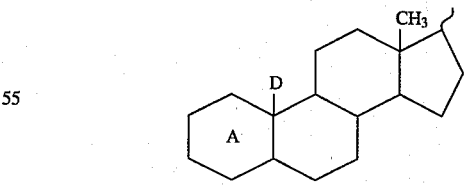

The material constituting a full disclosure of these compounds, their use and preparation is described in U.S. Pat. No. 5,196,542, issued 23 Mar. 1993, incorporated by reference herein.

CHART A
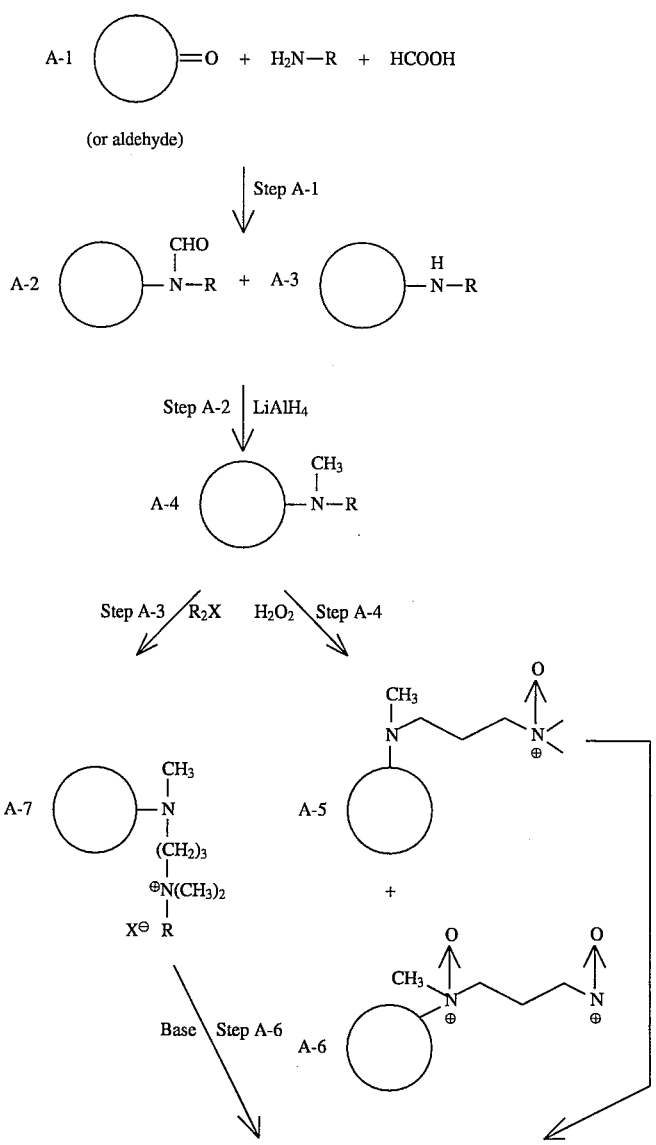

-continued
CHART A
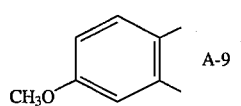
A-9
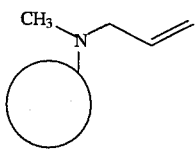
A-8
Step A-7 | Li/NH₃
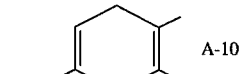
A-10
Step A-8 | H₃O⁺
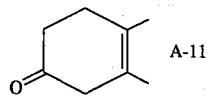
A-11
CHART B
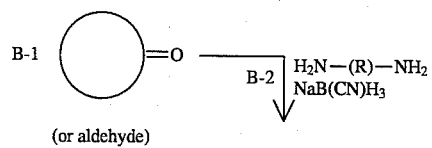
(or aldehyde)
Step B-1 | H₂N—R
         NaB(CH)H₃
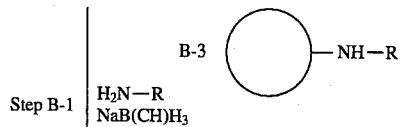
B-2
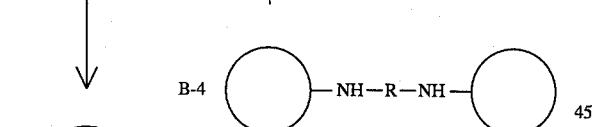
CHART C
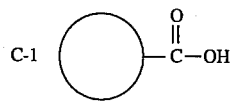
C-1
Step C-1 | SOCl₂
-continued
CHART C
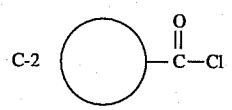
C-2
Step C-2 | NH₂—R
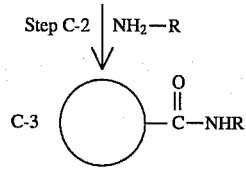
C-3
Step A-2 | LiAlH₄
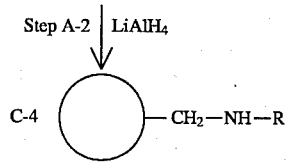
C-4
CHART D
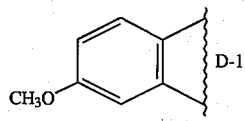
D-1
Step D-1 | (C₆H₅)₂—PH/n-C₄H₇Li -continued
CHART D

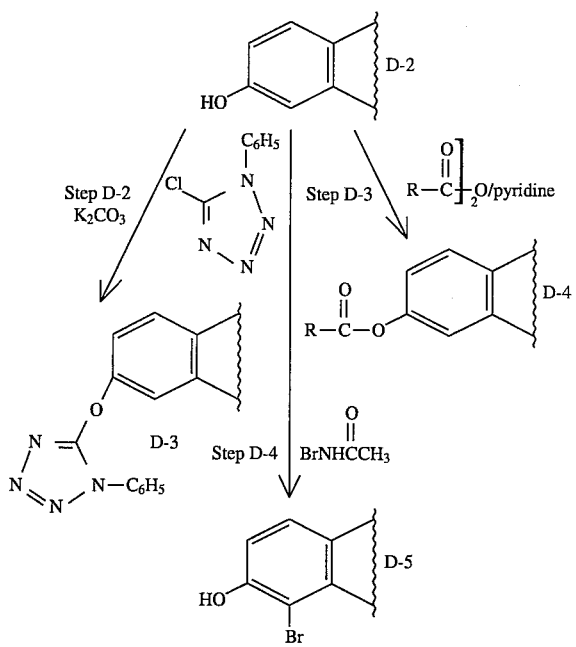

It is claimed:
1. A compound selected from the group consisting of:
a) 3-hydroxy-17β-(((3-trifluoromethyl)phenylmethyl) amino)-estra-1,3,5(10)-triene tetrahydrofuran solvate;
b) 3-methoxy-17β-((2-(4-chlorophenyl)ethyl)amino)-estra-1,3,5(10)-triene;
c) 3-(2,3-dihydroxypropoxy)-17β-((4-chlorophenylmethyl)amino)-estra-1,3,5(10)-triene;
d) 3-methoxy-17β-((4-methoxycarbonylphenylmethyl) amino)-estra-1,3,5(10)-triene;
e) 3-methoxy-17β-((4-bromophenylmethyl)amino)-estra-1,3,5(10)-triene;
f) 3-methoxy-17β-((3-chlorophenylmethyl)amino)-estra-1,3,5(10)-triene;
g) 3-methoxy-17β-((3-phenylpropyl)amino)-estra-1,3,5 (10)-triene;
h) 3-methoxy-17β-((4-phenylbutyl)amino)-estra-1,3,5 (10)-triene;
i) 3-methoxy-17β-((4-methylphenylmethyl)amino)-estra-1,3,5(10)-triene;
j) 3-methoxy-17β-((1-phenylethyl)amino)-estra-1,3,5 (10)-triene;
l) 3-methoxy-N-methyl-17β-(((3-trifluoromethyl)-phenylmethyl)amino)-estra-1,3,5(10)-triene;
m) 3-methoxy-N-ethyl-17β-(((3-trifluoromethyl)-phenylmethyl)amino)-estra-1,3,5(10)-triene;
n) 3-methoxy-N-(propyl)-17β-(((3-trifluoromethyl)phenylmethyl)amino)-estra-1,3,5(10)-triene;
o) 3-methoxy-N-(3-methylbutyl)-17β-(((3-trifluoromethyl)phenylmethyl)amino)-estra-1,3,5(10)-triene hydrochloride;
p) 3-methoxy-N-(octyl)-17β-(((3-trifluoromethyl)phenylmethyl)amino)-estra-1,3,5(10)-triene hydrochloride;
q) 3-methoxy-N-(tetradecyl)-17β-(((3-trifluoromethyl) phenylmethyl)amino)-estra-1,3,5(10)-triene;
r) 3-methoxy-N-ethyl-17β-((4-chlorophenylmethyl)-amino)estra-1,3,5(10)-triene;
s) 3-methoxy-N-ethyl-17β-((2-(4-aminosulfonylphenyl) ethyl)amino)-estra-1,3,5(10)-triene;
t) 3-methoxy-N-ethyl-17β-(((2-trifluoromethyl)phenylmethyl)amino)-estra-1,3,5(10)-triene;
u) 3-methoxy-N-(3-phenylpropyl)-17β-((3-phenylpropyl) amino)-estra-1,3,5(10)-triene;
and pharmacologically acceptable salts thereof.
2. A compound selected from the group consisting of
d) 17β-((2-(4-aminosulfonylphenyl)ethyl)amino)androstane;
e) (20s)-20-N-(3-trifluoromethyl)benzyl-19-norpregna-1, 3,5(10)-triene-20-amine.
3. A compound selected from the group consisting of:
q) N-benzyl-3-methoxyestra-1,3,5(10)-trien-17β-amine;
u) 17β-(phenylamino)androst-5-en-3α-ol hydrate;
w) 3-methoxy-17β-((4-chlorophenyl)amino)estra-1,3,5 (10)-triene;
x) 3-methoxy-17β-((4-methoxyphenyl)amino)estra-1,3, 5(10)-triene;
y) 3-methoxy-17β-(((3-trifluoromethyl)phenyl)amino) estra-1,3,5(10)-triene;
z) 3-methoxy-17β-((4-methoxycarbonyl)phenylamino) estra-1,3,5(10)-triene;
a1) 3-methoxy-N-17β-((phenylmethyl)amino)estra-1,3, 5(10)-triene;
b1) 3-methoxy-N-ethyl-17β-((phenylmethyl)amino) estra-1,3,5(10)-triene;
c1) 17β-9(phenylmethyl)amino)androst-5-en-3β-ol ethanol solvate;
d1) 17β-((2-furylmethyl)amino)androst-5-en-3β-ol;
e1) 17β-9(4-chlorophenylmethyl)amino)androst-5-en-3β-ol;
f1) 17β-((2-(4-aminosulfonylphenyl)ethyl)amino) androst-5-en-3β-ol;
h1) 17β-9((3-trifluoromethyl)phenylmethyl)amino) androst-5-en-3β-ol;
i1) 3-methoxy-17β-((4-chlorophenylmethyl)amino)estra-1,3,5(10)-triene;
j1) 3-methoxy-17β-(((3-trifluoromethyl)phenylmethyl) amino)estra-1,3,5(10)-triene;
k1) 3-methoxy-17β-((4-methoxyphenylmethyl)amino) estra-1,3,5(10)-triene;
l1) 3-methoxy-17β-(((4-trifluoromethyl)phenylmethyl) amino)estra-1,3,5(10)-triene;
n1) 3-methoxy-17β-((2-(4-aminosulfonylphenyl)ethyl) amino)estra-1,3,5(10)-triene;
o1) 3-methoxy-17β-(((4-aminosulfonylphenylmethyl) amino)estra-1,3,5(10)-triene;
q1) 3-methoxy-17β-(((2-trifluoromethyl)phenylmethyl) amino)estra-1,3,5(10)-triene;
s1) 3-methoxy-17β-((4-fluorophenylmethyl)amino)estra-1,3,5(10)-triene;
t1) 3-methoxy-17β-((3,4-dichlorophenylmethyl)amino) estra-1,3,5(10)-triene;
u1) 3-methoxy-17β-((2,4-dichlorophenylmethyl)amino)estra-1,3,5(10)-triene;
v1) 3-methoxy-17β-((2-chlorophenylmethyl)amino) estra-1,3,5(10)-triene;
b2) N-benzylestra-1,3,5(10)-trien-17β-amine;
c2) N-(3-trifluoromethylphenyl)-3-methoxyestra-1,3,5 (10)-trien-17β-amine;

d2) N-(4-methoxycarbonylphenyl)-3-methoxyestra-1,3,5(10)-trien-17β-amine;

and pharmacologically acceptable salts thereof.

4. A compound selected from the group consisting of:

c) N-diphenylmethyl-3-methoxyestra-1,3,5(10)-trien-17β-amine;

d) N-(2-(2'-phenyl)ethyl)-3-methoxyestra-1,3,5(10)-trien-17β-amine;

e) (1'S,2'S)-N-(1',3'-dihydroxy-1'-phenyl)isopropyl-3-methoxyestra-1,3,5(10)-triene-17β-amine;

f) N-(2'-(4"-hydroxyphenyl)ethyl)-3-methoxyestra-1,3,5(10)-triene-17β-amine;

g) N-benzyl-5α-androstan-17β-amine;

and pharmacologically acceptable salts thereof.

* * * * *